US00PP27079P3

(12) United States Plant Patent
Blackwell

(10) Patent No.: US PP27,079 P3
(45) Date of Patent: Aug. 23, 2016

(54) ***PISTACIA* ROOTSTOCK NAMED 'P.N.B.1'**

(50) Latin Name: *Pistacia intergerrima×Pistacia atlantica*
Varietal Denomination: P.N.B.1

(71) Applicant: Brian Blackwell, Avila Beach, CA (US)

(72) Inventor: Brian Blackwell, Avila Beach, CA (US)

( * ) Notice: Subject to any disclaimer, the term of this patent is extended or adjusted under 35 U.S.C. 154(b) by 126 days.

(21) Appl. No.: 14/120,980

(22) Filed: Jul. 18, 2014

(65) Prior Publication Data

US 2016/0021805 P1 Jan. 21, 2016

(51) Int. Cl.
*A01H 5/00* (2006.01)

(52) U.S. Cl.
USPC ..... Plt./152

(58) Field of Classification Search
USPC ..... Plt./152
See application file for complete search history.

*Primary Examiner* — Susan McCormick Ewoldt
(74) *Attorney, Agent, or Firm* — Cassandra Bright

(57) ABSTRACT

A new and distinct *Pistacia* cultivar named 'P.N.B.1' is disclosed, characterized by increased crop yield when used as a rootstock. Plants of the new variety are easier to produce in micropropagation, and grow faster under lower temperatures in the greenhouse. The new variety is a *Pistacia intergerrima×Pistacia atlantica,* produced as a commercial rootstock for grafting or budding onto.

3 Drawing Sheets

Latin name of the genus and species: *Pistacia intergerrima×Pistacia atlantica.*

Variety denomination: 'P.N.B.1'.

BACKGROUND OF THE INVENTION

The new cultivar is a product of a planned breeding program. The new variety resulted from an open pollination breeding program conducted in McFarland, Calif. The seed parent is an unpatented variety of, *Pistacia intergerrima× Pistacia atlantica.* The pollen parent is an unknown variety of *Pistacia intergerrima×Pistacia atlantica.* Date of the open pollination is unknown. The new variety was first selected in 2009, by the inventor, Brian Blackwell at a commercial nursery in McFarland, Calif.

Asexual reproduction of the new cultivar 'P.N.B.1' by vegetative cuttings was first in performed in 2009 at a commercial nursery in McFarland, Calif. and has shown that the unique features of this cultivar are stable and reproduced true to type on successive generations. Plants have also been reproduced via micropropagation. with consistent results.

SUMMARY OF THE INVENTION

The cultivar 'P.N.B.1' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'P.N.B.1'. These characteristics in combination distinguish 'P.N.B.1' as a new and distinct *Pistacia* cultivar:

1. Suitability for use as a rootstock upon which commercial nut bearing Pistachio varieties may be budded or grafted.
2. Easier to reproduce in tissue culture/micropropagation than known cultivars.

3. Greater production of "suckers" than known rootstock varieties
4. Faster growth under lower temperatures in a greenhouse.
5. Increased crop yield of commercial Pistachio production.

PARENT COMPARISON

Plants of the new cultivar 'P.N.B.1' are similar to plants of the seed parent in most horticultural characteristics, however, plants of the new cultivar 'P.N.B.1' differ in the following:

1. Plants of the new cultivar grow significantly more vigorously under field conditions.

COMMERCIAL COMPARISON

Plants of the new cultivar 'P.N.B.1' are similar to plants of the known commercial variety 'PN 15-4'. U.S. Plant Pat. No. 14,132, in most horticultural characteristics, however, plants of the new cultivar 'P.N.B.1' differ in the following:

1. Easier to reproduce in tissue culture/micropropagation than 'PN15-4'.
2. Greater production of "suckers"than 'PN 15-4'
3. Faster growth under lower temperatures in a greenhouse.
4. Increased crop yield of commercial Pistachio production of approximately 1.5 to 2%.

BRIEF DESCRIPTION OF THE PHOTOGRAPHS

The accompanying photograph in FIG. 1 illustrates in full color a typical plant of 'P.N.B.1' grown in a poly covered greenhouse, for the purpose of commercial rootstock production. Age of the plant photographed is approximately 1 year.

Figure 1:
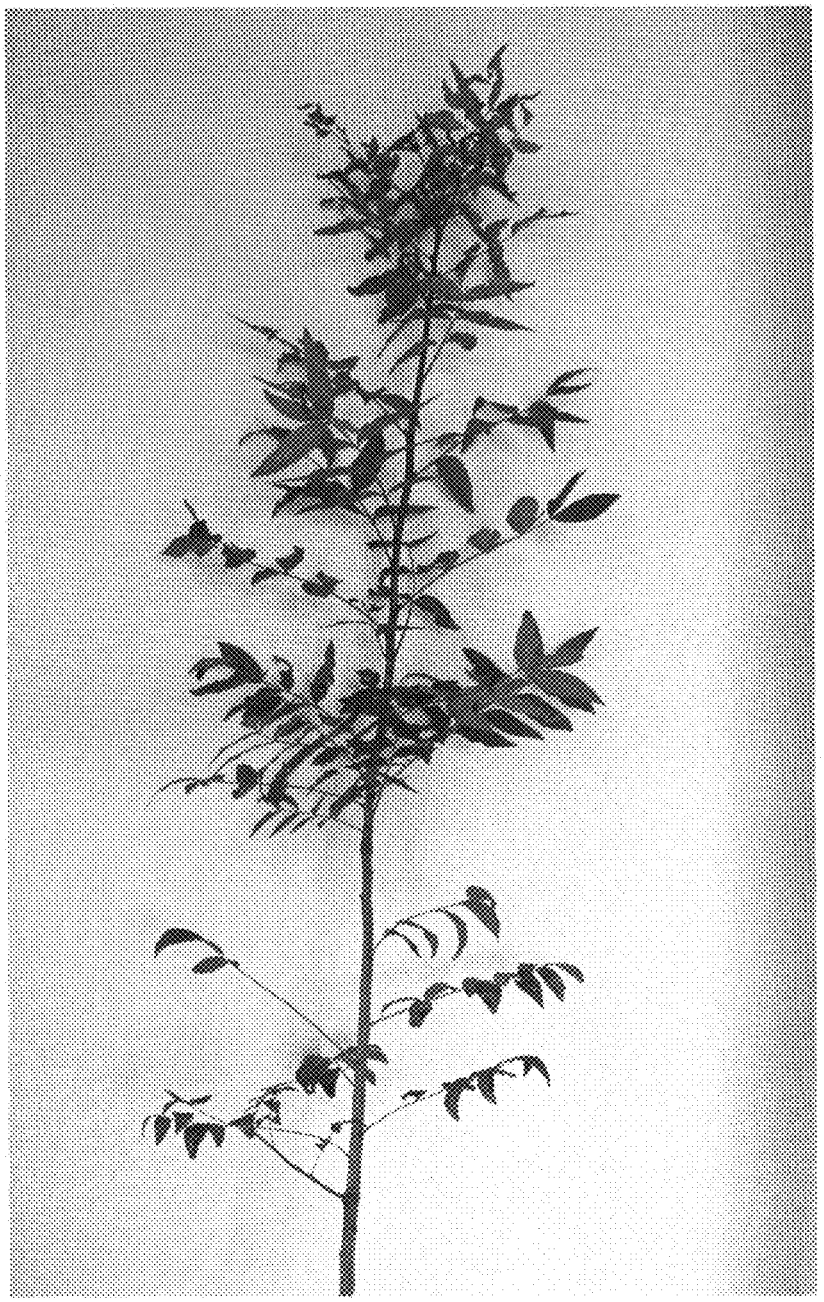
Figure 2:
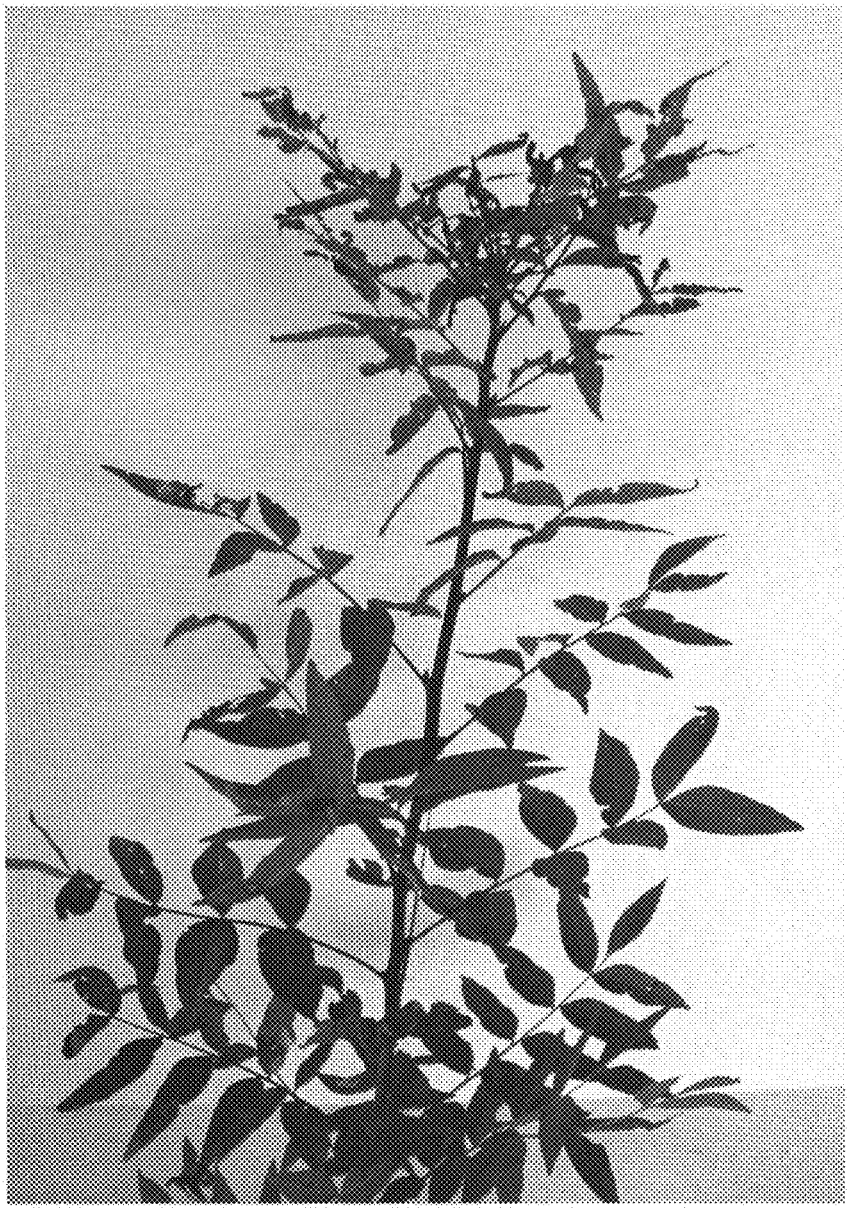
FIG. 2 illustrates in full a closer view of the stem and foliage of 'P.N.B.1'.
Figure 3:
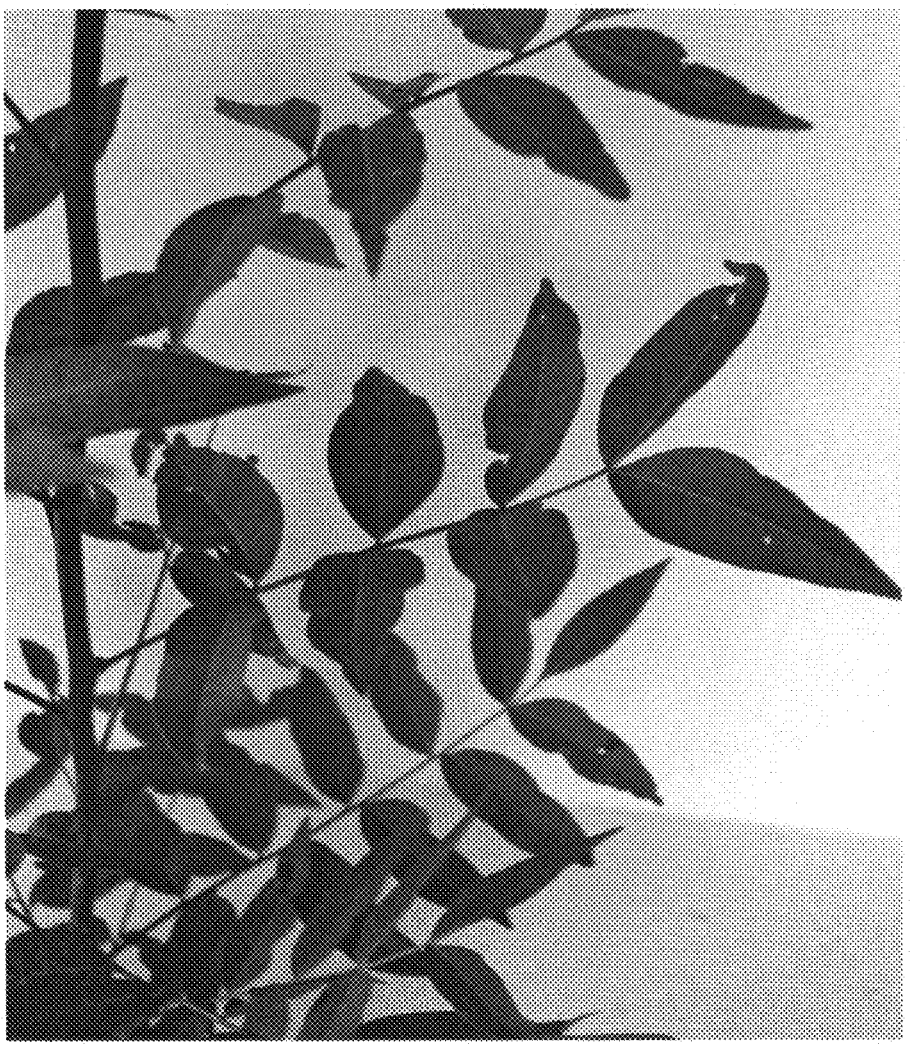
FIG. 3 illustrates a close up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'P.N.B.1' plants grown in a greenhouse in McFarland, Calif. Growing conditions are similar to USDA Zone 7. Age of the plants when described is approximately 1 year old. Measurements and numerical values represent averages of typical plant types.

Botanical classification: *Pistacia intergerrima*×*Pistacia atlantica* 'P.N.B.1'.

PROPAGATION

Time to initiate roots: About 60 days at approximately 21° C.

Time to produce a rooted cutting: About 120 days at 21° C.

Root description: Typical *Pistacia* root, thin, coarse, semi-woody roots, typically colored near RHS Grey-Brown 199A.

PLANT

Growth habit: Round medium to large deciduous tree.

Container size of tree described: 11 cm wide square nursery pot, with a depth of 20 cm.

Height: Approximately 140 cm.

Plant spread: Approximately 40 cm.

Branching characteristics: Not typically grown for above ground characteristics. Branches have not been observed to date. Compound leaves emerge from trunk on specimen measured.

Trunk:

- *Diameter*.—Approximately 1.5 cm after 1 year.
- *Texture*.—Semi-striated, rough.
- *Color*.—Striated near Grey-Brown 199A with Greyed-Orange N167A. Immature growth is colored near Greyed-Purple 187A with Greyed-Orange 177D dots.

Vegetative buds: Approximately 6 mm long and 4 mm wide. Colored near Yellow-Green N144C, heavily flushed Greyed-Purple 187A.

FOLIAGE

Leaf:

- *Arrangement*.—Alternate occurring compound leaves.
- *Compound leaf length*.—Average 20 cm.
- *Compound leaf width*.—Average 11 cm.

Leaflets:

- *Shape*.—Oblanceolate.
- *Quantity*.—Typically 9 or 11. Occurring in opposite pairs, with a single terminal leaflet.
- *Average overall length*.—6.5 cm.
- *Average overall width*.—2.0 cm.
- *Attachment*.—Sessile.
- *Apex*.—Acute.
- *Base*.—Blunt rounded.
- *Margin*.—Entire.
- *Texture of top surface*.—Glabrous, somewhat leathery.
- *Texture of bottom surface*.—Glabrous.
- *Pubescence*.—No leaf pubescence. Aspect: Flat to slightly undulating along margins.

Color:

- *Young foliage upper side*.—Background coloration near Yellow-Green 146C, heavily flushed with Greyed-Purple 183A, margins colored Greyed-Purple 187A.
- *Young foliage under side*.—Background coloration near Yellow-Green 146C, heavily flushed with Greyed-Purple 183A, margins colored Greyed-Purple 187A.
- *Mature foliage upper side*.—Green; near RHS 137A, but darker.
- *Mature foliage under side*.—Near RHS Green 137B.

Venation:

- *Type*.—Pinnate.
- *Venation color upper side*.—Yellow-green; near RHS 145A.
- *Venation color under side*.—Yellow-green; near RHS N144C.

Leaf petiole:

- *Length*.—4.5 cm.
- *Diameter*.—0.3 cm.
- *Color*.—Near RHS Greyed-Orange 177A.
- *Texture*.—Slightly pubescent.

Rachis:

- *Length*.—10 cm.
- *Diameter*.—0.2 cm.
- *Color*.—Near RHS Yellow-Green 146C, flushed Greyed-Orange 177A.
- *Texture*.—Slightly pubescent.

FLOWER

Flowering not observed to date.

REPRODUCTIVE ORGANS

Not observed to date.

OTHER CHARACTERISTICS

Seeds and fruits: The new cultivar does not produce seeds or fruit.

Disease/pest resistance: Neither resistance nor susceptibility to pathogens and pests common to *Pistacia* have been observed.

Temperature tolerance: The new variety is suitable for growing in USDA zones 7 through 11.

What is claimed is:

1. A new and distinct cultivar of *Pistachia* rootstock named 'P.N.B.1' as herein illustrated and described.

* * * * *